United States Patent [19]

Cooper et al.

[11] Patent Number: 4,742,388
[45] Date of Patent: May 3, 1988

[54] COLOR VIDEO ENDOSCOPE SYSTEM WITH ELECTRONIC COLOR FILTERING

[75] Inventors: David H. Cooper, Saratoga; Janos L. Hunyady, San Jose, both of Calif.

[73] Assignee: Fuji Photo Optical Company, Ltd., Omiya, Japan

[21] Appl. No.: 611,617

[22] Filed: May 18, 1984

[51] Int. Cl.⁴ ............................................... H04N 7/18
[52] U.S. Cl. ...................... 358/98; 358/29; 128/6
[58] Field of Search ............ 358/98, 901, 209, 1, 358/29, 29 C; 128/4-11

[56] References Cited

U.S. PATENT DOCUMENTS

| | | | |
|---|---|---|---|
| 3,375,388 | 3/1968 | Sheldon | 358/98 X |
| 4,007,488 | 2/1977 | Morishita et al. | 358/29 C |
| 4,074,306 | 2/1978 | Kakinuma et al. | 128/6 X |
| 4,253,447 | 3/1981 | Moore et al. | 358/98 X |
| 4,532,918 | 8/1985 | Wheeler | 358/98 X |

OTHER PUBLICATIONS

"Handy Endoscopic Color TV System Using New Chalnicon Pickup Tube", Fukui et al.; Toshiba Review, #97, pp. 24–29.

Primary Examiner—James J. Groody
Assistant Examiner—Victor R. Kostak
Attorney, Agent, or Firm—Michael L. Harrison

[57] ABSTRACT

A color video endoscope system including a light source, color wheel and light guide for directing sequential fields of red, green and blue (RGB) light into a cavity, a solid state image sensor for transmitting a signal in response to the intensity of the reflected fields of light, a video processor for converting the signal from the image sensor into a composite RGB video signal compatible with a color monitor, and a plurality of electronic color filters for altering the true color of the image on the monitor.

9 Claims, 3 Drawing Sheets

COLOR VIDEO ENDOSCOPE SYSTEM WITH ELECTRONIC COLOR FILTERING

BACKGROUND OF THE INVENTION

This invention relates to a color video endoscope system, and in particular to an endoscope system having electronic color filtering to alter the true color of the image presented on the monitor.

Various color video endoscope systems are described in U.S. Pat. No. 4,253,447 to Moore and U.S. Pat. No. 4,074,306 to Kakinuma. Such systems include a control unit which generates alternating fields of red, green, and blue (RGB) light. The light is directed through a fiber optic light guide within a separate endoscope section which plugs into the control unit and which has a viewing head for insertion into the cavity to be viewed. The light reflected from the cavity into which the viewing head is inserted is received by a solid state image sensor in the viewing head. The image sensor transmits an electrical signal back to the control unit in response to the intensity of light reflected within the cavity from the sequential color fields. The signal is processed according to its separate red, green, and blue components by the control unit and then later merged into a composite RGB video signal compatible with a monitor.

In such color video endoscope systems it is often desirable or necessary to filter certain colors of the light. For example, fluorescein dye is often injected into a patient and absorbed by certain tissue. This particular dye is an excellent reflector of blue light so that if other colors are filtered out from the image on the monitor, the particular tissue under study will be emphasized. In another application of color filtering, it may desirable to give the appearance that the light within the cavity is incandescent light so that indoor film can be used to take a photograph of the image on the monitor. This effect can be accomplished by filtering out portions of the blue and green light in order to give an orange tint to the image. In still another application, it may be desirable to take a "polaroid" photograph of the image on the monitor, in which case it is necessary to slightly increase the blue light by reducing the amount of red and green light from the image.

In conventional color video endoscopes, color filtering is accomplished mechanically in various ways by altering the color of the light entering the cavity. For example, if it is desirable to create a blue image, then only blue light is directed through the fiber light guide and into the cavity by placing a blue filter in the light path. The conventional system of filtering light has several inherent disadvantages. First, because the light is filtered with optical color filters placed in front of the light source, only a discrete number of filter combinations are available. Thus, while it would be possible to utilize a blue filter so that only blue light entered the cavity, it would not be possible to select any particular shade or intensity of blue light. In addition, the filters are subject to damage and degradation by being placed for substantial periods of time in front of the light source.

SUMMARY OF THE INVENTION

The invention is a color video endoscope system for use in displaying a color image from inside a cavity onto a monitor, and includes means for electronically filtering colors from the image on the monitor by altering the electronic signal transmitted from the image sensor during the processing of the signal by the control unit.

The color video endoscope system of the present invention includes a light source, color wheel and light guide for generating and delivering sequential color fields of red, green and blue light into the cavity, an image sensor having active light-responsive elements for receiving the reflected image from the cavity and generating sequential electrical signals corresponding to the sequential color fields of light, a video processor for processing the signals received from the image sensor into a composite RGB video signal for display as a color image on the monitor, and means for altering each of the portions of the signal from the image sensor corresponding to the sequential color fields in the video processor so as to vary the color of the image on the monitor.

In the preferred embodiment, the means for altering the signal in the video processor includes separate potentiometers, each of whose output is applied to a respective portion of the signal corresponding to a color field. Each potentiometer is connected to a gate prior to its input to the video processor, and the appropriate gates are turned on and off by timing circuitry which is synchronized with the sequential color fields generated by the color wheel. Thus, as each portion of the signal from the image sensor passes into the video processor, the proper gate is turned on to apply a particular gain to that portion of the signal, the gain level being set by the potentiometer associated with that particular color field. In the preferred embodiment there are three groups of potentiometers, each group corresponding to the signal for each of the three color fields, and means for selecting one of the potentiometers from each group. In this manner a plurality of color filter combinations can be manually selected in the control unit by a switch which selects one of the potentiometer outputs from each of the groups. Thus, for example, if switch position for "filter 1" on the control unit is connected to a potentiometer at zero setting for the red signal, a potentiometer at zero setting for the green signal, and a potentiometer at maximum setting for a blue signal, the signal output by the video processor will be a signal corresponding to only blue color fields and the image on the monitor will be blue.

The above-described means for selecting combinations of electronic color filters in the color video endoscope system also functions in conjunction with circuitry which supplies fixed image sensor-dependent gain levels to the video processor. Each image sensor, even image sensors of the same type, possesses unique characteristics of voltage level output in response to direct, unreflected light of the three primary colors. Thus, if no color filtering is desired so that the image on the monitor is to be the true color, these fixed image sensor-dependent gain levels must be applied to the video processor so that a true color image appears on the monitor. The electronic color filtering means of the present invention is capable of operation with the circuitry which applies these fixed image sensor-dependent gain levels to the video processor.

For a fuller understanding of the nature and advantages of the invention, reference should be made to be ensuing detailed description taken in conjunction with accompanying drawings.

DESCRIPTION OF THE PREFERRED EMBODIMENTS

Figure 1:
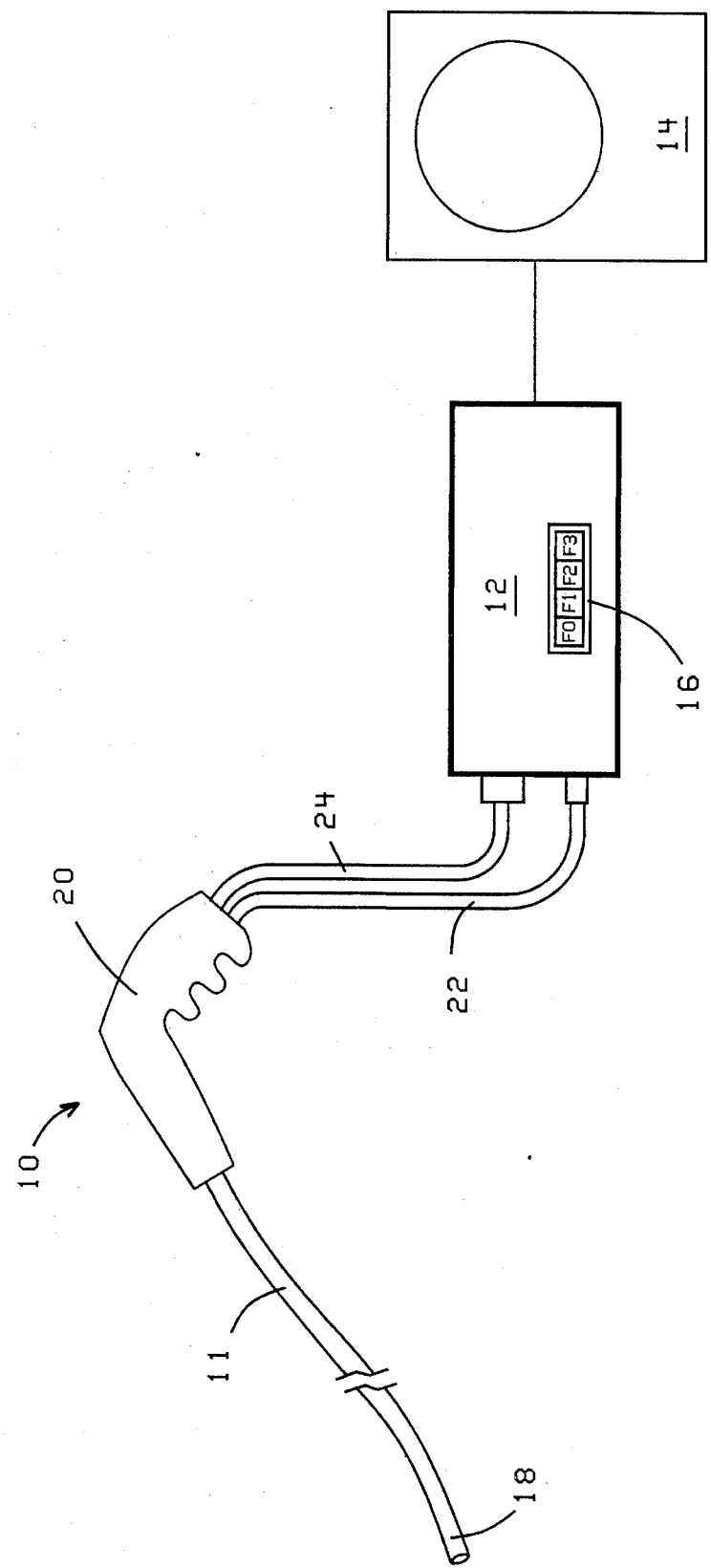
FIG. 1 is a simplied diagram illustrating the endoscope, monitor, and control unit with switches for selecting combinations of color filters.

Referring first to the simplified diagram of FIG. 1, the color video endoscope system includes generally an endoscope section 10 and a control unit 12. The control unit 12 provides an RGB video output signal to a monitor 14 for display of the image. The endoscope section 10 includes an insertion tube 11 having a viewing head 18 at its distal end, an operating section 20 for control of the endoscope by the user, an electrical connector 22 between the operating section 20 and the control unit 12, and a mechanical connector 24 between the operating section 20 and control unit 12. Sequential color fields of light supplied by a light source and a color wheel in the control unit 12 pass through a fiber optic light guide through connector 24, operating section 20, insertion tube 11 and viewing head 18. Included in the viewing head 18 of the endoscope 10 is the image sensor and the lens assembly for directing and focusing the reflected color fields of light from the cavity back to the image sensor. An electrical connection is made between the image sensor and the control unit 12 through an electrical connector in insertion tube 11 between viewing head 18 and operating section 20 and through electrical connector 22. The viewing head 18 also includes circuitry to buffer the electrical pulses from the control unit 12 which trigger the image sensor to transfer its output data and to amplify the output signal from the image sensor back to the control unit 12. The signal from the image sensor, which is a signal having sequential portions corresponding to the color fields of light, is transmitted to the video processor where electronic color filtering occurs, the color filtering being selected by switches of the filter selector 16 on control unit 12.

Figure 2:
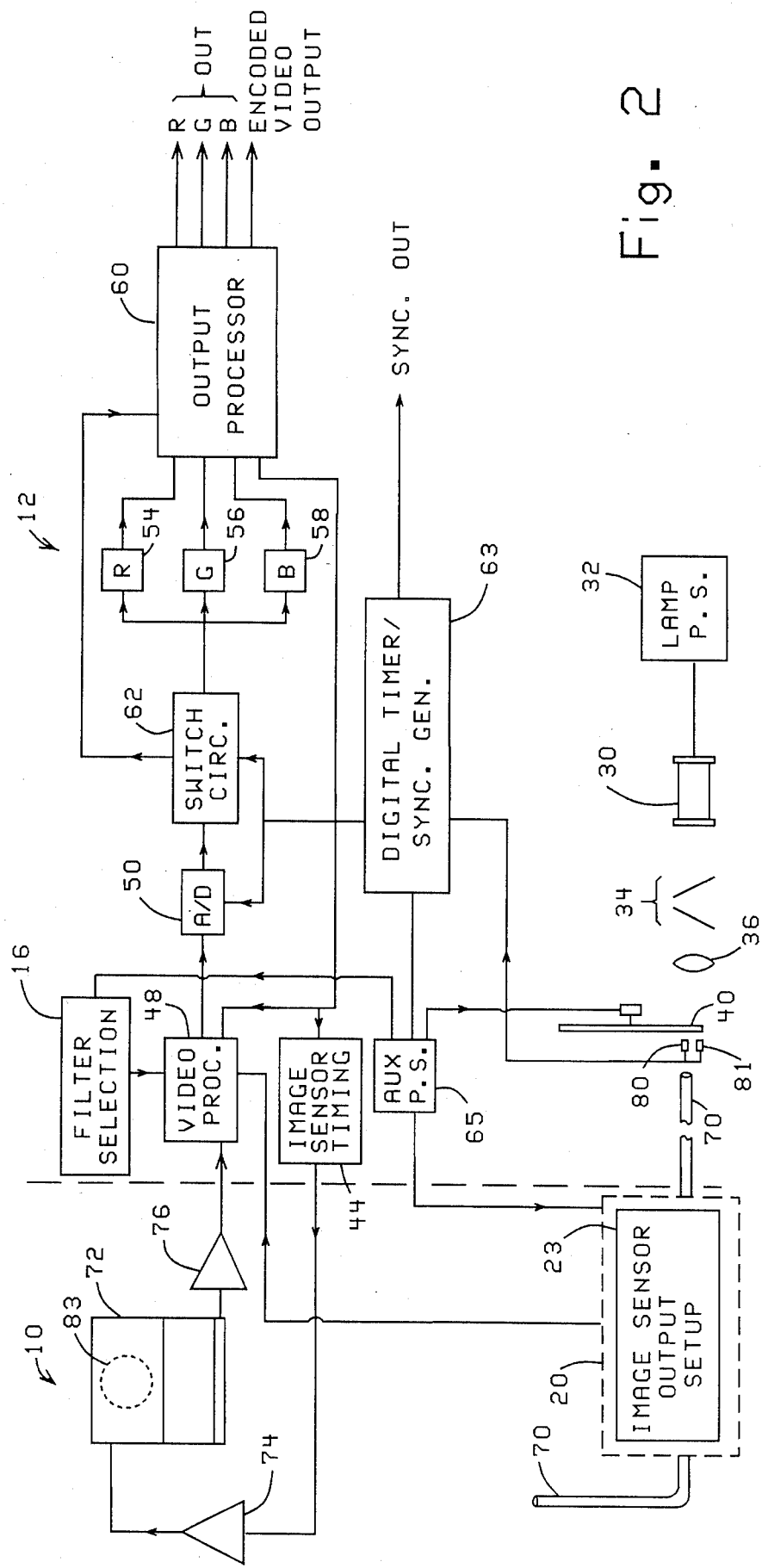
FIG. 2 is a block diagram of the control unit with filter selection circuitry and the endoscope with the image sensor output setup circuitry.

The above explanation of the color video endoscope system can be further understood by reference to the block diagram in FIG. 2, wherein the primary components of control unit 12 and endoscope 10 are illustrated. Control unit 12 comprises a light source 30 and power supply 32, a color wheel 40, a digital timer/sync generator 63, an auxiliary power supply 65, image sensor timing circuitry 44, video processor 48 which receives the output signal from the image sensor, filter selection circuitry 16 coupled to video processor 48 for altering the signal from the image sensor to vary the true color of the image presented to the monitor, analog/digital (A/D) converter 50, memory storage units 54, 56, 58 for receiving and temporarily storing data corresponding to image sensor output for the respective color fields of light, an output processor 60 for generating RGB and encoded video signals in which data corresponding to the color fields appears simultaneously, and switching circuitry 62 for controlling the data corresponding to the color fields to the output processor 60.

The endoscope 10 includes a fiber optic light guide 70 for directing light into the cavity, an operating section 20 including image sensor output setup circuitry 23, an optical focusing assembly (not shown) in the viewing head 18 (FIG. 1) for focusing the reflected light, an image sensor 72, buffer circuitry 74 between the image sensor timing circuitry 44 and the image sensor 72, and output signal driving circuitry 76 between image sensor 72 and video processor 48.

The general operation of the color video endoscope system with electronic color filtering can be better understood by explaining the specific function of the above-described components during operation. The light source 30, which is typically a xenon short-arc lamp, receives power from lamp power supply 32 and transmits light through a pair of infrared filters 34, a lens 36 and color wheel 40 into the input end of the fiber optic light guide 70. The color wheel 40 contains circular segments of alternating red, blue and green color filters and opaque circular segments located between the color filter segments. The color wheel 40 is rotated at a constant speed controlled by sync generator 63 so that each filter segment completely traverses the light path within approximately 1/60th of a second. As illustrated in FIG. 2, a pair of light sensitive devices, such as photodiodes 80, 81, are aligned in the light path and oriented at the perimeter of color wheel 40. Located around the perimeter of color wheel 40 is a pattern of opaque and transparent sections which rotate through the light path in which the diodes 80, 81 are aligned. One or both of the photodiodes 80, 81 will produce output or no output as the pattern passes, depending upon which color field is in proximity to them. With this arrangement, it is possible to provide a signal to the digital timer 63 to synchronize the rotation of color wheel 40 with the operation of video processor 48, which is receiving signals from image sensor 72 corresponding to the respective color fields.

As the color wheel 40 rotates, alternating fields of red, green and blue light are sequentially passed into light guide 70 and thus into the cavity where the viewing head 18 of the endoscope insertion tube 11 is located. This colored light is then reflected and focused by the lens assembly (not shown) in the viewing head onto image sensor 72. As shown in FIG. 2, the output of the lens assembly focuses a pattern designated by circular line 83 onto image sensor 72. Thus, for approximately 1/60th of a second the image sensor 72 has received red light and generated electrical charges in its various cells corresponding to the amount of red light energy received by each cell. As the color wheel 40 continues to rotate, a blank segment passes in front of light source 30 and no light enters the light guide 70 or the cavity. During this blanking interval, the data stored in the image sensor 72 is shifted out serially through driver circuitry 76 and ultimately to the video processor 48. The image sensor timing circuitry 44, which is controlled by the master timer 63, pulses the image sensor 72 during this blanking interval, thereby clocking the data out of the image sensor 72. Simultaneously, the video processor 48 receives a signal from the master timer 63 to transfer data corresponding to one color field out to the A/D converter 50 and ultimately to one of the memory storage devices 54, 56, 58, so that the video processor 48 may receive data from the image sensor 72 corresponding to the next color field. As shown in FIG. 2, there are three memory storage devices, each of which is preferably a dynamic random access memory (DRAM), for storing digital data corresponding to the output signal for one particular color field from image sensor 72. The switching circuitry 62, which is similarly controlled by digital timer 63, alternately triggers data to be transferred from A/D converter 50 into the respective DRAMs. The switching circuitry 62 also includes means for simultaneously transferring data corresponding to one color field from A/D converter 50 both to its respective DRAM and directly to output processor 60. Thus the output processor 60 generates a composite RGB video signal by taking data from two color fields prior in time out of their DRAMs and combining this data with the data from one color field which has been transferred directly from the switching circuitry 62. The output processor 60 provides an RGB output which is fully compatible with a color monitor.

Figure 3:
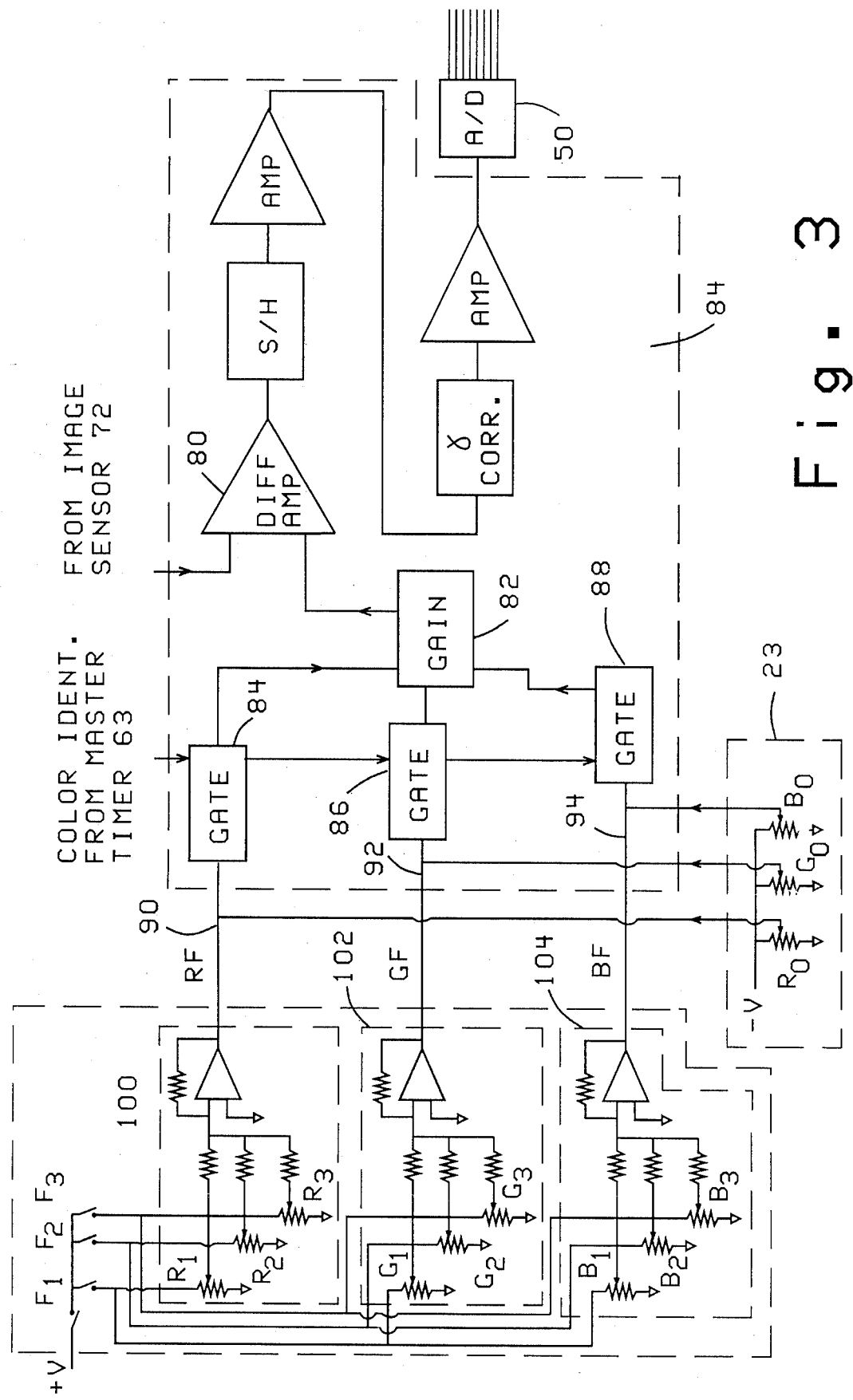
FIG. 3 is a block diagram of the video processor illustrating the electronic color filtering circuitry and the circuitry for applying the fixed image sensor-dependent gain levels.

Referring now to FIG. 3, the operation of the image sensor output setup circuitry 23 and the electronic filter selection circuitry 16 to modify the operation of video processor 48 will be explained. The gain applied to differential amplifier 80 in video processor 48 is dependent upon two inputs, a fixed image sensor-dependent gain from image sensor output setup circuitry 23 and the gain from filter selection circuitry 16, both of which are input to gain control circuitry 82. Even without any electronic color filtering, the amount of gain necessary to optimize the red, green and blue characteristics of the image sensor 72 is different for each color field. Particular reference voltage levels from potentiometers R0, G0 and B0 are applied to the gain control circuitry 82 from the image sensor output setup circuitry 23 through gates 84, 86, 88 respectively. As red, green, or blue color field data is transferred to amplifier 80 from image sensor 72, a signal from the color identification circuitry in the sync generator 63 (FIG. 1) turns on the appropriate gate 84, 86 or 88, thereby setting the gain control circuitry 82 to the proper present level according to the correct color field. In this manner, and without any color filtering, the signal processed and output to the monitor is the true color viewed by the image sensor since the proper amount of gain, corresponding to the image sensor's sensivity to direct unreflected red, green and blue light, are applied to the signal during processing.

As shown in FIG. 3, the filter selection circuitry 16 includes three identical gain generation circuits 100, 102 and 104 for the generation of red gain RF on line 90, green gain GF on line 92, and blue gain BF on line 94. The values of RF, GF and BF which are input to gates 84, 86 and 88 respectively, depend upon which potentiometers from the respective groups, e.g. R1, R2 or R3 are selected and the settings of those selected potentiometers. The combination of red, green and blue potentiometers is selected by switches F1, F2 and F3, each of which corresponds to a predetermined color filter. Switch F0 is the "normal" setting, which when opened indicates that no color filtering is being applied to the signal. While not illustrated in FIG. 3, the switches F0, F1, F2 and F3 are mechanically interlocked so that the opening or closing of one of the switches also opens or closes the other switches. For example, the closing of switch F1 to make contact with potentiometers R1, G1 and B1 automatically closes switch F0 and opens switches F2 and F3. In a similar manner, the opening of switch F0 to select no color filtering automatically opens switches F1, F2 and F3. The switches are operable from the exterior of control unit 12 (FIG. 1) and allow the user to select true color of the image of the monitor by opening switch F0, and three other color filters controlled by switches F1, F2 and F3. Each of the filter selection switches permits a unique combination of red, green, and blue gains to be applied to the corresponding signal components from image sensor 72 during operation of video processor 48. The amount of gain RF, GF and BF applied to video processor 48 when any one of the switches F1, F2 or F3 is selected depends upon the position of the settings of the potentiometers in each of the groups. For example, if it is desired to have switch F2 create a filter which gives the appearance of incandescent light within the cavity, then it is necessary to give an orange tint to the image on the monitor by taking out some of the green and blue gain. This would be accomplished by reducing green and blue gain levels below their true color levels by setting potentiometers G2 and B2 below their normal values, while leaving potentiometer R2 at its normal setting. These adjustments once made within control unit 12, are not altered, so that selecting switch F2 automatically creates an incandescent filter.

The operation of the filter selection circuitry 16 and the image sensor output setup circuitry 23 through the series of gates 84, 86 and 88 to apply gain to the signal components received from image sensor 72 will now be explained. Assume for purposes of explanation that switch F0 designates no color filtering, so that the image on the monitor is the true color, and that switch F1 designates a fluorescein blue filter. If switch F0 is open, then switches F1, F2 and F3, which are mechanically interlocked with switch F0, are also open. The voltage levels on output lines 90, 92 and 94 will all be zero since no gain is generated by any of the color gain circuits 100, 102 or 104. The only contribution to gain will be from image sensor output circuitry 23, namely the fixed voltage levels which have been preset in the endoscope by potentiometers R0, G0 and B0. As the signal is being processed by video processor 48, the color identification circuit from sync generator 63 alternately clocks gates 84, 86 and 88 so that only the proper gain R0, G0 or B0 is applied to gain control circuitry 82 at the time that the corresponding portion of the signal from image sensor 72 is being applied to differential amplifier 80. As each portion of the signal corresponding to a respective color field is received in differential amplifier 80, a specific gain is applied because the color identification circuit has triggered the proper gate to close and the other gates to open.

If in the present example it is now desired to alter the image on the monitor from the true color to a fluorescein blue, then switch F1 is closed, which thereby makes contact with the potentiometers R1, G1 and B1 of the respective gain generation circuits 100, 102 and 104. The closing of switch F1 automatically closes switch F0 and opens switches F2 and F3. There is now presented on lines 90, 92, and 94 respective filter gain settings RF, GF and BF, which are summed with the gain settings from potentiometers R0, G0 B0 of image sensor output circuitry 23. In designing the proper settings for the potentiometers R1, G1 and B1 in order to obtain a fluorescein blue image, the gain for potentiometer R1 is set to cancel out the gain for potentiometer R0, and the gain for potentiometer G1 is set to cancel out the gain for potentiometer G0. In this manner the total gain input into gate 84 for the red color field signal will be zero. Similarly the total gain input into gate 86 for the green color field signal will be zero. The potentiometer B1 will be set at its maximum level so that the gain BF output from the blue gain circuitry 104 will be at its maximum level and will be summed with the gain for potentiometer B0 for input into gate 88. As the sequential signal from image sensor 72 enters differential amplifier 80, the color identification circuit in sync generator 63 will triggers gates 84, 86 and 88 in succession to apply the respective gain levels to gain control circuit 82. During that period of time when a red component of the signal and a green component of the signal is being processed through differential amplifier 80, there will be no gain applied, and thus no red or green signal will be output by video processor 48. During that period of time when the blue component of the signal from image sensor 72 is being processed, gate 88 will be triggered to input the sum of the voltage levels from line 94 and from potentiometer B0 to gain control circuitry 82, so that the maximum level of gain will be applied to the blue signal component in differential amplifier 80. In this manner, only data corresponding to blue light will be output by video processor 48 and the image appearing on the monitor will be a fluorescein blue image.

Thus, with the present invention it is possible to program multiple electronic color filters. It should also be apparent that if so desired it is possible to change the function of one of the filters, such as filter F1, by simply altering the potentiometer settings R1, G1, and B1. It should further be apparent that the above-described preferred embodiment is only one means of providing electronic color filtering to the color video endoscope system. For example, it would be possible to alter the respective portions of the sequential signal which have originated from the image sensor after the signal has been converted to a digital signal, that is, after the signal has passed through A/D converter 50. This could be accomplished by a timing circuitry controlled by the color identification circuitry of sync generator 63, and a series of registers containing variable digital values which could be summed with the digital signal from A-D converter 50.

While the preferred embodiments of the present invention have been illustrated in detail, it should be apparent that modifications and adaptations of those embodiments will occur to those skilled in the art. However, it is to be expressly understood that such modifications and adaptations are within the sphere and scope of the present invention as set forth in the following claims.

What is claimed is:

1. A color video endoscope system for use in displaying an image produced by light reflected from objects inside a cavity on a monitor, comprising:
   means for generating and delivering sequential color fields of light;
   an image sensor having a field of view for sensing light reflected from objects within the cavity and for producing an electrical signal in response to the intensity of light received, the electrical signal having sequential components corresponding to the reflected light;
   processing means, electrically coupled to the image sensor for sequentially processing the signal components from the image sensor into a video signal, for presentation of an image on the monitor; and
   means electrically coupled to the image sensor signal processing means for altering the signal components in the processing means so as to alter the color of the image on the monitor.

2. The color video endoscope system according to claim 1 wherein the signal component altering means includes means for altering the gain for each of the signal components in the processing means.

3. The color video endoscope system according to claim 1 wherein the signal component altering means includes means for removing all but one of the signal components corresponding to all but one of the color fields so as to create a single-color image on the monitor.

4. In a color video endoscope system of the type having means for generating sequential fields of red, green, and blue light into a cavity, an image sensor for generating a sequential signal in response to the sequential fields of color light reflected from within the cavity, and means electrically coupled to the image sensor for processing the sequential signal into a true color image displayed on a monitor, an improvement for electronically filtering light from the true color image on the monitor comprising means electrically coupled to the processing means for applying a specific gain to each portion of the sequential signal from the image sensor corresponding to a particular color field.

5. The improved color video endoscope system according to claim 4 wherein the gain application means further comprises means for selecting one of a number of combinations of preset gains to be applied to the portions of the sequential signal corresponding to red, green, and blue light.

6. The improved color video endoscope system according to claim 5 wherein the selection means further comprises means for individually varying each of the preset gains.

7. In a color video endoscope system of the type having means for generating sequential fields of red, green, and blue light into a cavity, an image sensor for generating a signal having sequential components corresponding to the light from the color fields reflected from within the cavity, and means electrically coupled to the image sensor for converting the sequential signal components from the image sensor into a video signal for presentation of a color image on a monitor, an improvement to the color video endoscope system comprising:
   means for applying one of a plurality of preset voltage levels to the red signal component;
   means for applying a fixed image sensor-dependent voltage level to the red signal component;
   means for applying one of a plurality of preset voltage levels to the green signal component;
   means for applying a fixed image sensor-dependent voltage level to the green signal component;
   means for applying one of a plurality of preset voltage levels to the blue signal component;
   means for applying a fixed image sensor-dependent voltage level to the blue signal component;
   means for summing the preset voltage level and the fixed image sensor-dependent voltage level for each of the red, green and blue signal components;
   a plurality of gates, each gate being electrically coupled between the means for summing the voltage levels applied to a corresponding signal component and the signal component conversion means;
   timing means electrically coupled to each of the gates for sequentially connecting the summed voltage levels to be applied to each of the signal components to the signal component conversion means in synchronization with the red, green and blue signal components transmitted by the image sensor to the signal component conversion means; and means electrically coupled to the red, green and blue preset voltage level applications means for selecting one of a plurality of combinations of red, green and blue preset voltage levels, each combination corresponding to a predetermined color filter effect on the monitor.

8. The improved color video endoscope system according to claim 7 further comprising means for adjusting each of the preset voltage levels to be applied to each of the red, green and blue signal components, whereby the color filter effects corresponding to the combinations of red, green and blue preset voltage levels may be changed.

9. A color video endoscope system for use in displaying an image produced by light reflected from objects inside a cavity on a monitor, comprising:

means for generating and delivering sequential color fields of light;

an image sensor having a field of view for sensing light reflected from objects within the cavity and for producing an electrical signal in response to the intensity of light received, the electrical signal having sequential components corresponding to the reflected light;

processing means, electrically coupled to the image sensor for sequentially processing the signal components from the image sensor into a video signal, for presentation of an image on the monitor;

means electrically coupled to the image sensor signal processing means for altering the signal components in the processing means so as to alter the color of the image on the monitor;

means electrically coupled to the processing means for transmitted to the processing means a fixed gain level for each signal component in the processing means, the fixed gain levels being predetermined image sensor-dependent levels to create a true color image on the monitor;

timing means electrically coupled to the processing means and the fixed gain level transmitting means for applying each of the fixed gain levels to the proper signal component corresponding to the proper sequential color field, and;

means electrically coupled to the processing means for summing each of the fixed gain levels with the gain altered for each of the signal components by the signal altering means.

* * * * *